US012557985B2

(12) United States Patent
Dellagiacoma et al.

(10) Patent No.: US 12,557,985 B2
(45) Date of Patent: Feb. 24, 2026

(54) DEVICE AND METHOD FOR MEASURING AT LEAST ONE GEOMETRIC PARAMETER OF THE EYE

(71) Applicant: Haag-Streit AG, Köniz (CH)

(72) Inventors: Claudio Dellagiacoma, Bern (CH);
Frank Zumkehr, Zollikofen (CH)

(73) Assignee: Haag-Streit AG, Köniz (CH)

( * ) Notice: Subject to any disclaimer, the term of this patent is extended or adjusted under 35 U.S.C. 154(b) by 1101 days.

(21) Appl. No.: 17/442,947

(22) PCT Filed: Mar. 26, 2019

(86) PCT No.: PCT/EP2019/057627
§ 371 (c)(1),
(2) Date: Sep. 24, 2021

(87) PCT Pub. No.: WO2020/192899
PCT Pub. Date: Oct. 1, 2020

(65) Prior Publication Data
US 2022/0202287 A1     Jun. 30, 2022

(51) Int. Cl.
*A61B 3/02*          (2006.01)
*A61B 3/024*        (2006.01)
(Continued)

(52) U.S. Cl.
CPC ............... *A61B 3/107* (2013.01); *A61B 3/13* (2013.01); *A61B 3/14* (2013.01)

(58) Field of Classification Search
CPC ......... A61B 3/02; A61B 3/102; A61B 3/1025; A61B 3/113; A61B 3/1015; A61B 3/1005; A61B 3/0083; A61B 3/1225; A61B 3/024
See application file for complete search history.

(56) References Cited

U.S. PATENT DOCUMENTS 5,790,233 A     8/1998  Ulbers et al.
6,120,444 A  *  9/2000  Miyakawa ............. A61B 3/165
                                                          600/401
(Continued)

FOREIGN PATENT DOCUMENTS

DE     102014210786     12/2015
JP       2004-351151      12/2004
JP       2012-187178      10/2012

OTHER PUBLICATIONS

Int'l Search Report (Form PCT/ISA/210) conducted in Int'l Application No. PCT/EP2019/057627 (Jan. 13, 2020).
(Continued)

*Primary Examiner* — Dawayne Pinkney
(74) *Attorney, Agent, or Firm* — GREENBLUM & BERNSTEIN, P.L.C.

(57)                    ABSTRACT

In order to measure at least one geometric parameter of an eye, Purkinje reflections from blue and infrared light sources are recorded with a microscope and a camera. Due to the dispersion of the optics of the microscope, at least one set of reflections is defocused. By measuring the radii of the reflections, the offset of the camera from an ideal focusing position or another distance parameter can be calculated. The distance parameter can e.g. be used to correct the magnification factor of the microscope even if the microscope is a non-telecentric microscope. For example, it can be used to carry out more accurate keratometry measurement using a non-telecentric microscope and/or non-telecentric illumination.

24 Claims, 5 Drawing Sheets

(51) Int. Cl.
| | |
|---|---|
| *A61B 3/10* | (2006.01) |
| *A61B 3/107* | (2006.01) |
| *A61B 3/12* | (2006.01) |
| *A61B 3/13* | (2006.01) |
| *A61B 3/14* | (2006.01) |

(56) References Cited

U.S. PATENT DOCUMENTS

| | | | |
|---|---|---|---|
| 10,888,457 B2 * | 1/2021 | Artsyukhovich | A61B 3/0091 |
| 2011/0105943 A1 * | 5/2011 | De Paz Sicam | A61B 3/0025 |
| | | | 600/558 |
| 2015/0150448 A1 * | 6/2015 | Takii | A61B 3/152 |
| | | | 351/208 |
| 2017/0258320 A1 | 9/2017 | Abreu | |
| 2018/0160899 A1 * | 6/2018 | Brown | G02B 5/0263 |
| 2019/0142269 A1 * | 5/2019 | Copland | A61B 3/18 |
| | | | 351/206 |
| 2019/0307325 A1 * | 10/2019 | Eil | G01B 11/25 |

OTHER PUBLICATIONS

Int'l Written Opinion (Form PCT/ISA/237) conducted in Int'l Application No. PCT/EP2019/057627 (Jan. 13, 2020).

\* cited by examiner

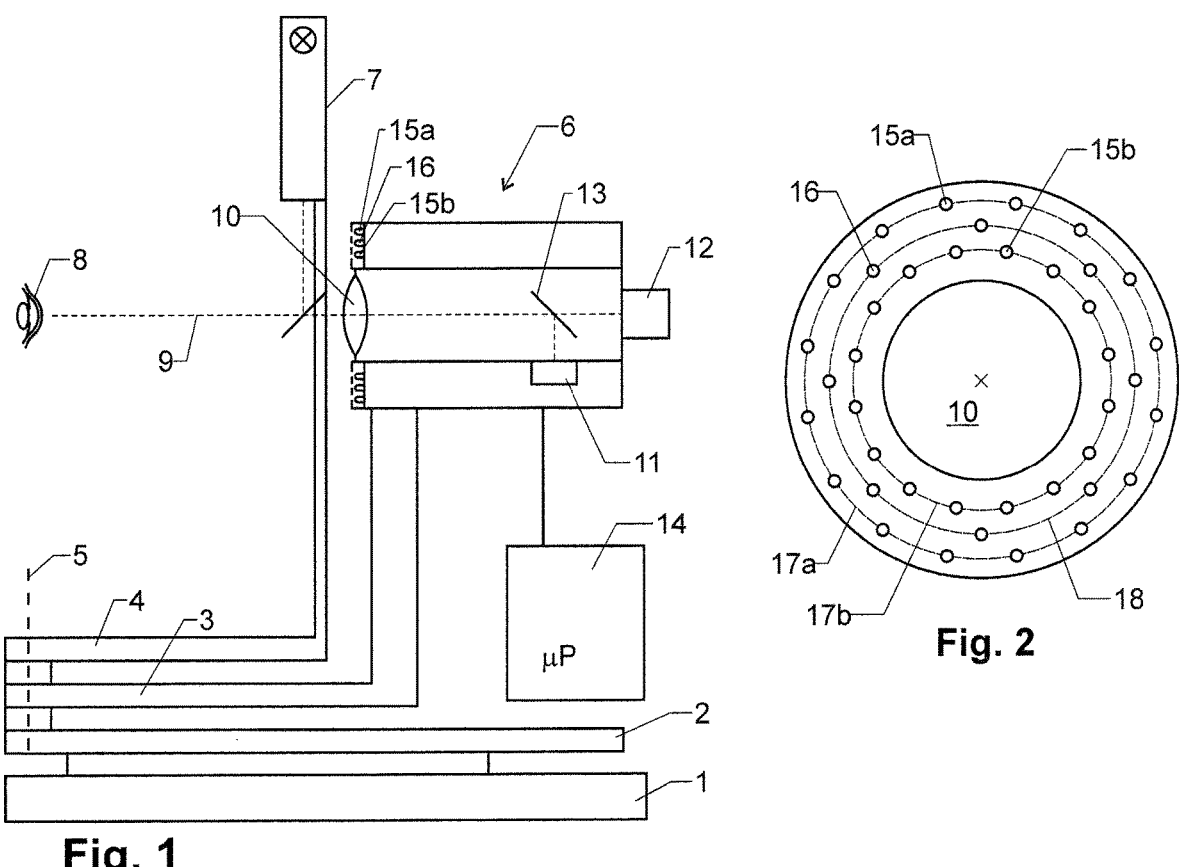
Fig. 1
Fig. 2
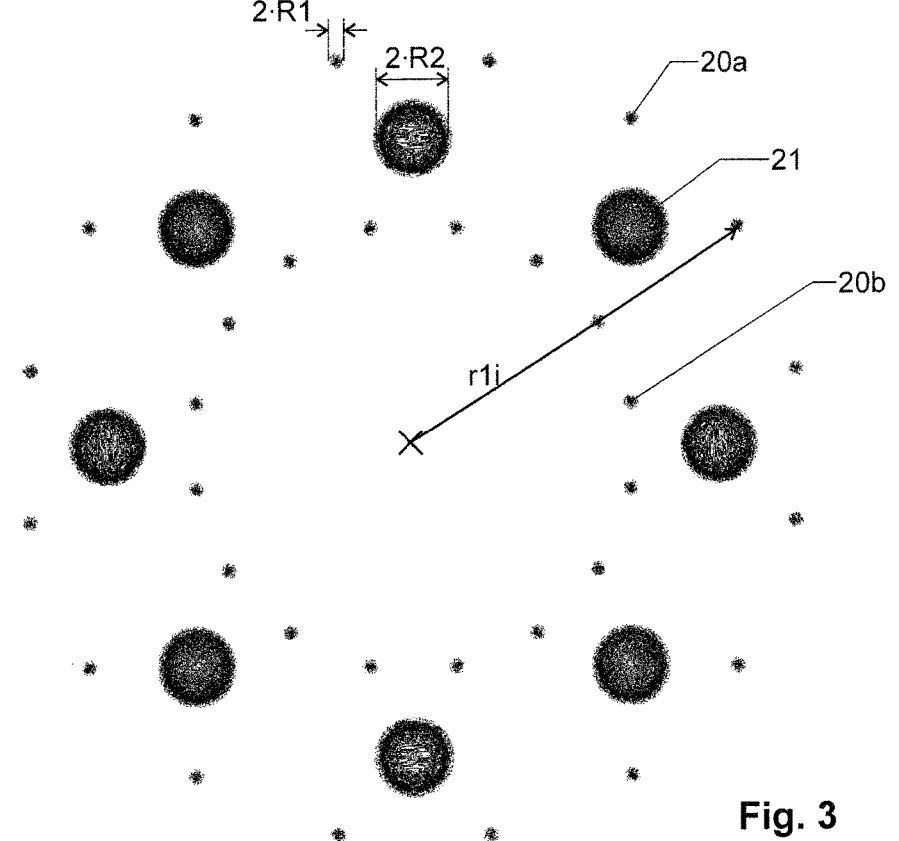
Fig. 3

DEVICE AND METHOD FOR MEASURING AT LEAST ONE GEOMETRIC PARAMETER OF THE EYE

TECHNICAL FIELD

The invention relates to a device and method for measuring at least one geometric parameter of the eye. In particular, it relates to a device and method for carrying out a keratometric measurement on the eye, i.e. for measuring at least one curvature of the anterior surface of the cornea.

BACKGROUND ART

Optically measuring a geometric parameter of the human eye usually requires the distance between the microscope and the eye to be known.

This is particularly true for keratometric measurements where the curvature of the cornea is to be measured from a Purkinje image such as described in U.S. Pat. No. 5,790,233.

It is also true for many other applications where a geometric parameter of the eye is to be measured using a non-telecentric microscope, e.g. when measuring the size of a structure in a picture of the eye.

Also, a quantitative analysis of Placido rings requires either telecentric illumination and microscopy or knowledge of the distance between the microscope and the eye.

For accurate measurements, this distance has to be measured because it varies even if a headrest or similar device is used for defining the subject's position.

In another approach, such as described in DE102014210786, complex, large telecentric microscopes and illumination systems are used to make the measurement less sensitive on the distance between the eye and the microscope.

DISCLOSURE OF THE INVENTION

The object of the present invention is to provide a method and device of this type that are simple and show improved accuracy.

This object is achieved by the method and device of the independent claims.

In particular, the invention relates to a method for measuring at least one geometric parameter of an eye using a device having a microscope. The method comprises at least the following steps (in any reasonable order):

Sending light having a first wavelength onto said eye: This light is to generate a first reflection.

Sending light having a second wavelength different from the first wavelength onto said eye: This light is to generate a second reflection. The term "wavelength" designates the wavelength of maximum intensity of the light. The two wavelengths being different is advantageously understood such that the difference of the wavelengths is at least five times the sum of the spectral full width half maximum (FWHM) of the light sources. In particular, said difference is at least 100 nm, in particular at least 300 nm, for the reasons explained below.

Viewing the eye through the microscope and recording at least a first reflection from the first light and at least a second reflection from the second light: In other words, the reflections of the light from the eye are observed by means of the microscope. Since the reflections have different wavelengths and the optics of the microscope is subject to optical dispersion, at least one of them is slightly defocused. This affects the width of the observed reflections.

Measuring at least one of a first width parameter indicative of a width of said first reflection and/or at least a second width parameter indicative of a width of said second reflection: In this context, the "width" of the reflection is advantageously a diameter or radius of the reflection in a given direction. It may e.g. also be the width of an edge region of the reflection. The measurement can e.g. be carried out in the coordinates of the photograph, i.e. the camera.

Using the first and/or the second width parameter for calculating a distance parameter depending on a distance between said microscope and said eye: This step exploits the fact that at least one of the reflections will be defocused. As described below, the degree of defocusing (which directly affects the respective width parameter) depends on the distance between the eye and the microscope.

Recording a geometry image depending on the geometric parameter and on the distance: This is the image used for measuring the desired geometric parameter, such as a curvature of the cornea's anterior surface. It may be the same image as it was used for measuring the first and/or second width parameter (the reference image), or it may be a different image.

Calculating the geometric parameter using the geometry image and the distance parameter: In this step, the knowledge of the distance parameter is used to correct for the distance-dependence of the geometry image and allows to calculate the geometric parameter more accurately.

In another aspect, the invention relates to a device for measuring at least one geometric parameter of an eye comprising:

A microscope: The microscope can be used to observe the eye.

One or more light sources: These emit light at first and second wavelengths, wherein said second wavelength is different from said first wavelength.

A camera mounted to said microscope: The camera is adapted and structured to record the image of the eye as obtained by the microscope.

A control unit: This control unit is adapted and structured for carrying out the steps of the method as described here.

The distance parameter may be indicative of (i.e. describing) the distance between the microscope from a position where it would be focused optimally on the first or on the second reflection.

Advantageously, the distance parameter is calculated using the difference between the first and the second width parameter. As explained below, this difference is nearly proportional to the difference between the actual position of the microscope and an ideal focusing position thereof.

If the first and second reflection are recorded together in a "reflection image" (i.e. in a single image), they are guaranteed to have been obtained for the same distance and microscope settings, and their analysis yields more accurate results.

Advantageously, the "reflection image" and the "geometry image" are the same images. This simplifies the measurement and makes it more accurate.

Advantageously, the microscope is focused onto the first reflection while recording the first and second reflection. In this case, the first width parameter should be small while the second width parameter (or its difference to the first width parameter) will almost linearly depend on the difference between the actual position of the microscope and an ideal focusing position thereof.

Advantageously, the distance parameter is calculated from the first and/or second width parameter using calibration data, e.g. stored in the device's control unit. Such calibration data may have been obtained from measuring the first and/or second width parameter for a plurality of distances of the microscope from a reference sample having e.g. a spherical surface.

The first and second light may be generated with one or more light sources emitting at both wavelengths, such as with white LEDs. In this case, a spectrally selective camera is advantageously used for recording two separate image channels, one for the first wavelength and the other for the second wavelength.

Alternatively, the device may comprise at least one first light source emitting light at the first wavelength and at least one second light source emitting light at the second wavelength.

For more accurate measurements, there may be several first and/or several second light sources for the light of the first and second wavelength, giving rise to several first and/or second reflections, and several first and/or second width parameters are derived by analyzing the individual reflections. The several light sources may e.g. be evenly distributed around the optical axis of the microscope.

The invention is advantageously used for keratometric measurements, in which case the geometric parameter is a local curvature of the anterior surface of the cornea.

BRIEF DESCRIPTION OF THE DRAWINGS

The invention will be better understood and objects other than those set forth above will become apparent when consideration is given to the following detailed description thereof. This description makes reference to the annexed drawings, wherein:

FIG. 1 shows a lateral view of a slit lamp microscope,

FIG. 2 shows a front view of the microscope as seen from the eye to be examined, FIG. 3 shows a Purkinje image recorded by the microscope (dark pixels correspond to bright areas)

MODES FOR CARRYING OUT THE INVENTION

Figure 4:
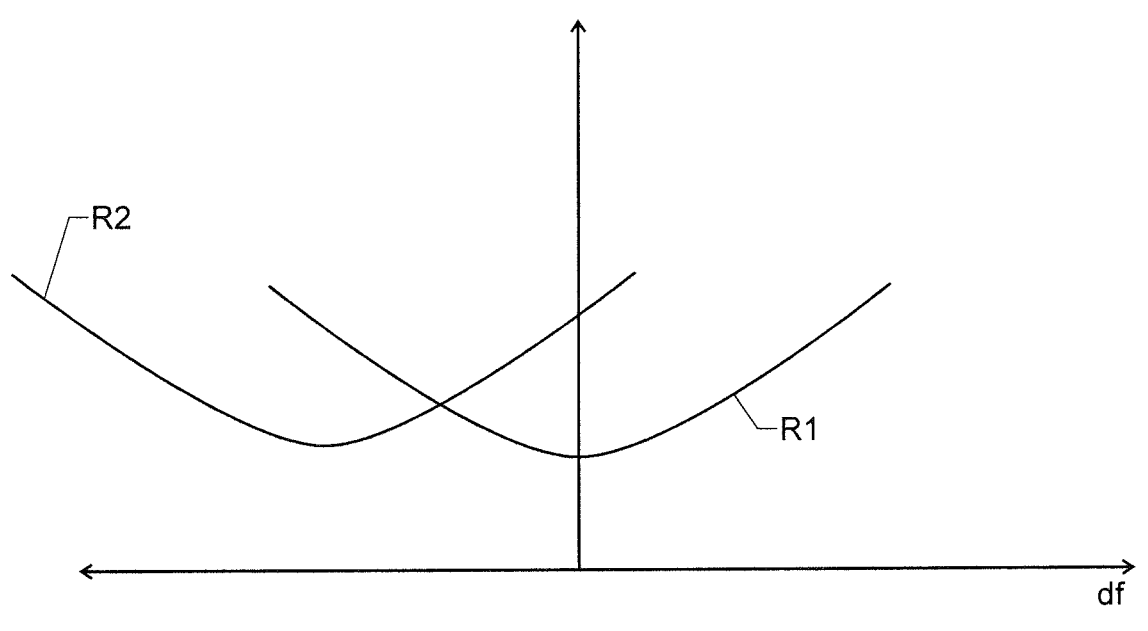
FIG. 4 shows the radii of the first and second reflection in the Purkinje image as a function of the distance between the eye and the microscope.

Device:

FIGS. 1 and 2 show an embodiment of a device designed as a slit lamp microscope. The device comprises a base 1 resting e.g. on a desk, a horizontally and vertically displaceable stage 2 mounted to base 1, a first arm 3, and a second arm 4.

The arms 3 and 4 are mounted to stage 2 and pivotal about a common vertical pivot axis 5.

The device may further include a headrest mounted to base 1 for receiving the patient's head.

Arm 3 carries a microscope 6 and arm 4 a slit illumination 7.

Slit illumination 7 is optional. It may e.g. be a conventional slit lamp as known to the skilled person, adapted to project a slit-shaped light beam onto the eye 8 to be examined.

Microscope 6 has an optical axis 9 intersecting with pivotal axis 5. It may comprise an entry objective 10 forming part of conventional, non-telecentric imaging optics, which projects an image of eye 8 onto a camera 11 and/or an eyepiece 12.

For quantitative measurements, the device advantageously is equipped with camera 11, while eyepiece 12 is optional. A beam splitter 13 may be arranged to spilt light between these components.

A plurality of first light sources 15a, 15b and second light sources 16 are arranged on microscope 6 and movable together with it. Advantageously, they are located around entry objective 10 and/or on a side of microscope 6 that faces eye 8.

The light sources 15a, 15b, 16 may be arranged radially outside entry objective 10. This simplifies the design of the device. The effects of the non-telecentric illumination resulting from this arrangement can be compensated as described below.

In the present embodiment, the first light sources 15a, 15b are arranged on at least a first circle 17a and a second circle 17b, with at least three of the first light sources on each circle.

The second light sources 16 are arranged on a third circle 18, with the circle 18 arranged advantageously between the circles 17a, 17b of the first light sources 15a, 15b.

All circles are concentric and perpendicular to optical axis 9 of microscope 6.

In more general terms, a plurality of the first light sources and/or the second light sources are advantageously arranged on at least one circle.

This arrangement in circles simplifies the analysis of the Purkinje reflections as described below and delivers curvature radii of eye 8 in various directions.

In the present embodiment, the first and second light sources 15a, 15b, 16 are point light sources. In particular, the diameter of each first and/or second light source is at least 100 times, in particular at least 1000 times smaller than the distance between eye 8 and microscope 6. Their structure cannot be resolved by microscope 6 even if microscope 6 it is perfectly focused on one of their reflections.

Advantageously, the first and/or second light sources are LEDs. They may, however, also be other types of light sources, e.g. semiconductor lasers.

Advantageously, the first light sources 15a, 15b may be infrared light sources with a wavelength of at least 800 nm.

The second light sources may e.g. have a wavelength of less than 500 nm any may e.g. emit blue light.

The wavelengths of the first and second light sources 15a, 15b, 16 is advantageously chosen such that the focal length of the optical system is as different as possible, but they should both be recordable by camera 11.

The device further comprises a control unit 14, e.g. a microprocessor, which is connected at least to camera 11. It may contain a memory with the programming to carry at least part of the processing steps described here and/or the calibration values mentioned below.

Operation:

In operation, slit illumination 7 is not necessarily used and may e.g. be pivoted away.

The first and second light sources 15a, 15b, 16 are activated.

As mentioned above, the first and second light sources 15a, 15b, 16 differ in their wavelengths.

Since the optics of camera 6 is subject to optical dispersion, it will not be able to exactly focus on the reflections of both types light sources at the same time. If, for example, it is focused in the reflections 20a, 20b of the first light sources 15a, 15b, the reflections 21 of the second light sources 16 will remain unfocused. This is illustrated in the image shown in FIG. 3 where the radii R1 of first reflections 20a are smaller than the radii R2 of the second reflections 21.

Without limitation, it is assumed that the microscope is focused on the first reflections 20a, 20b. Such focusing can be done manually or by machine control, and it is typically not perfect.

Figure 6:
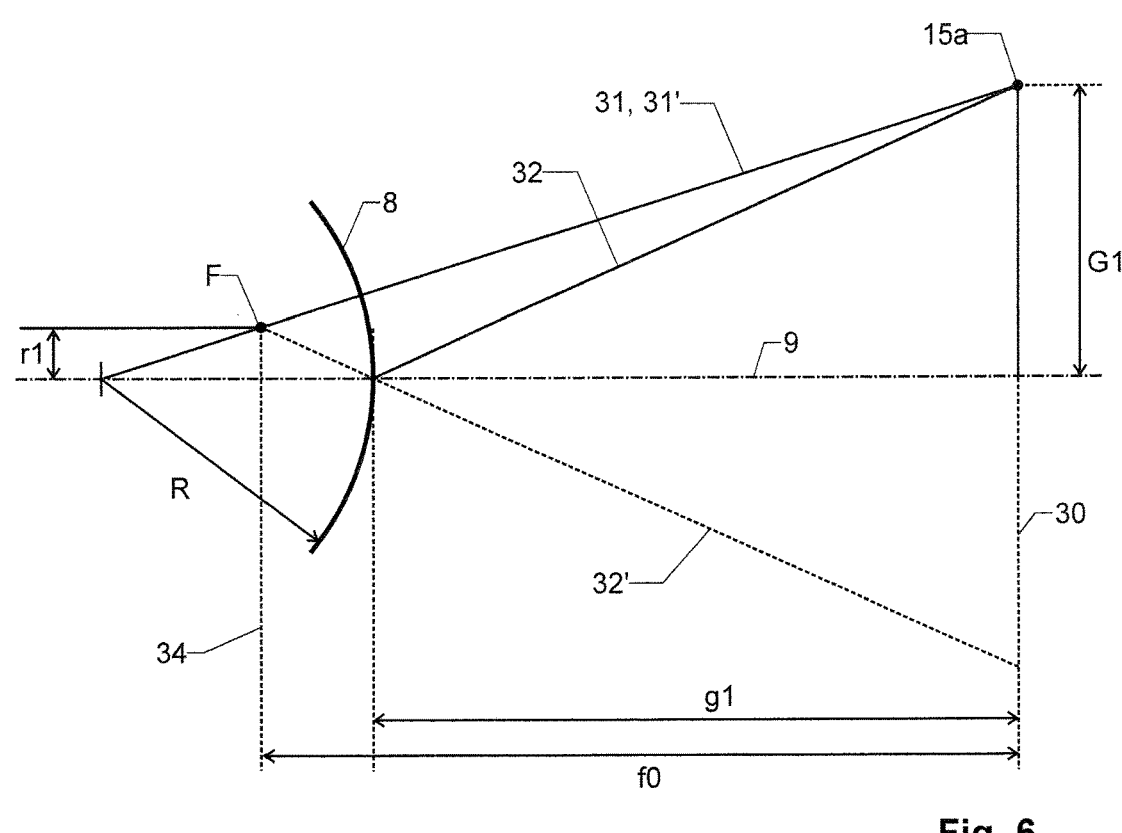
FIG. 6 illustrates the geometry giving rise to the Purkinje reflections.

FIG. 6 shows the geometry giving rise to the Purkinje reflections under ideal focusing conditions for a single first light source 15a.

In this example, it is assumed that the light source lies in a plane 30 perpendicular to optical axis 9, and this plane is used to define the 'position' of microscope 6.

31, 32 illustrate two light beams emitted from light source 15a and impinging on eye 8, which is assumed to be spherical.

Light beam 31 impinges perpendicular on the eye's surface and therefore is reflected therefrom into itself, i.e. its reflection 31' coincides with the original beam 31.

Light beam 32 impinges on the eye's apex, i.e. where the eye's surface is vertical. Its reflection 32' is therefore, in view of the horizontal optical axis 9, symmetric to light beam 32.

F denotes the intersection of the lines representing the reflections 31', 32'.

In good approximation, point F is the 'virtual light source' created by reflecting light source 15a on the surface of eye 8.

When microscope 6 is focused perfectly on the reflection (i.e. on point F), point F lies in the microscope's focal plane 34.

When the magnification factor of microscope 6 is known (i.e. the scaling factor between the coordinates of in the image recorded by camera 11 and the real distances in the microscope's focal plane 34), it is possible to determine the distance r1 of point F from optical axis 9 by measuring the distance r1i (in image coordinates) of its reflection from the center in the Purkinje image of FIG. 3.

At perfect focusing, distance r1 of point F from optical axis 9 is a function of The ideal focal distance f0, which is a known property of the device;

The distance G1 of light source 15a from optical axis 9, which is also known;

The Radius R of the anterior surface of the cornea of eye 8.

Hence, once the value r1 has been determined knowing the magnification factor of microscope 6, R can be calculated as $$R = R(r1, G1, f) \qquad (1)$$

The skilled person is familiar with the methods to calculate function R(r1, G1, f).

In approximation, assuming that all reflected light beams originating from light source 15a coincide at point F, we have $$R = 2 \cdot r1 \cdot f0 \cdot G1 / (G1^2 - r1^2) \qquad (2)$$

This follows from the lens equation for thin lenses applied for a virtual image (q<0) of a convex mirror with focal length f=−R/2:

$$\frac{1}{f} = \frac{1}{p} + \frac{1}{q} \qquad (2a)$$

and magnification $$\frac{r_1}{G_1} = m = -\frac{q}{p}, \qquad (2b)$$

where $p = g_1$ is the object distance and $q = g_1 - f_0$ the virtual image distance (see e.g.: Hecht, Eugene (2002). Optics (4th ed.). Addison Wesley, ISBN 978-0-321-18878-6).

Eq. (1) or (2) can be solved for any of the reflections 20a, 20b, 21 in the Purkinje image of FIG. 3 by measuring the radius r1 from r1i using the known magnification of microscope 6.

By measuring the radius r1 for a plurality of the reflections, as they are shown in FIG. 3, it is possible to determine the aspheric properties of the anterior surface of the corona of eye 8.

Distance Correction:

As mentioned, a microscope's magnification M in its focal plane is typically known, e.g. from calculations or calibration measurements. In this case, $$r1 = M \cdot r1i \qquad (3)$$

with r1i being the radius measured in the image of camera 11.

In practice, however, focusing on the reflection, i.e. on point F, is not perfect, i.e. the microscope's focal plane 34 and point F may not coincide.

Figure 7:
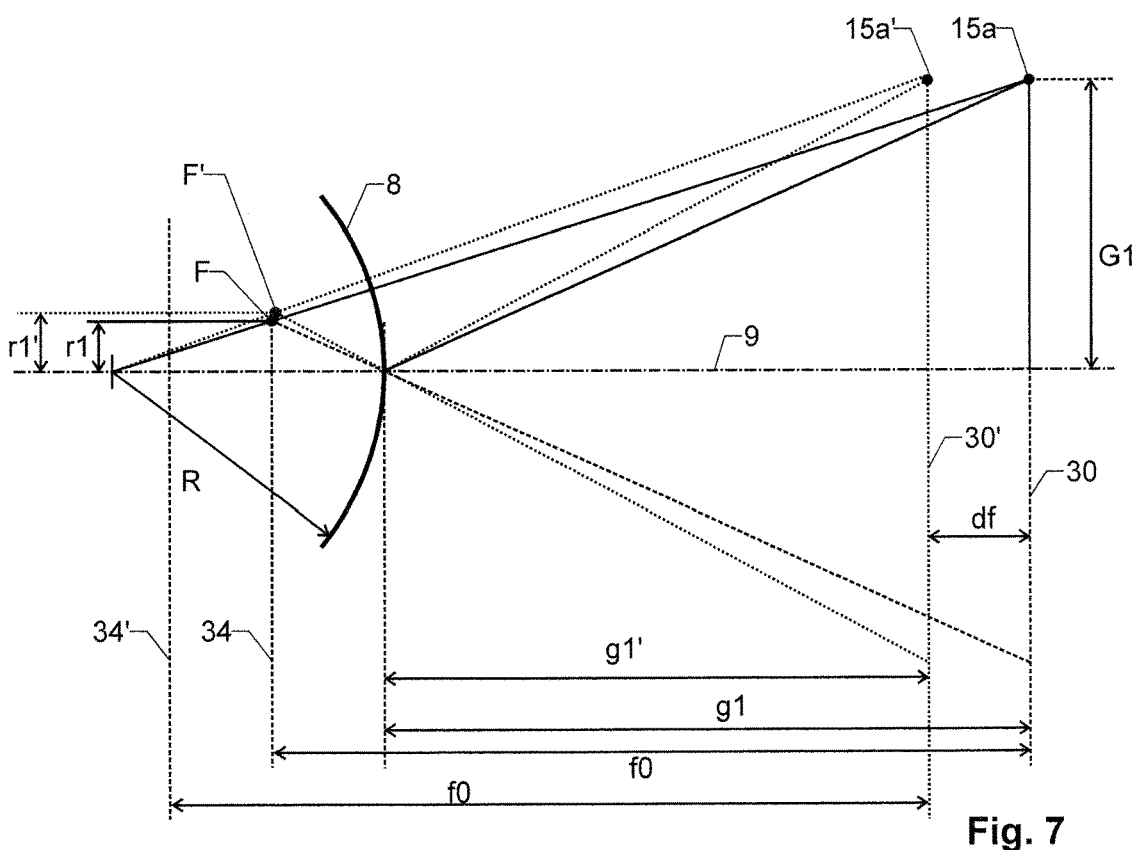
FIG. 7 illustrates the influence of the eye-microscope distance on the geometry of FIG. 6.

FIG. 7 illustrates a situation where the microscope has moved by a length df from the ideally focused position 30 to a defocused position 30'. It shows, in dotted lines, the light beams from the light source 15a' of the offset microscope.

Such a defocusing has two effects that affect the measurement:

1) Since the illumination from light source 15a, 15a' is non-telecentric, the location of point F changes to point F'. In particular, the distance r1 changes to a new distance r1'.

2) Further, the focal plane 34' of the microscope moves away from point F. Since microscope 6 is non-telecentric, such defocusing will not only affect the diameter of the reflections received in camera 11 but also cause the image of point F to be displaced radially.

Figure 10:
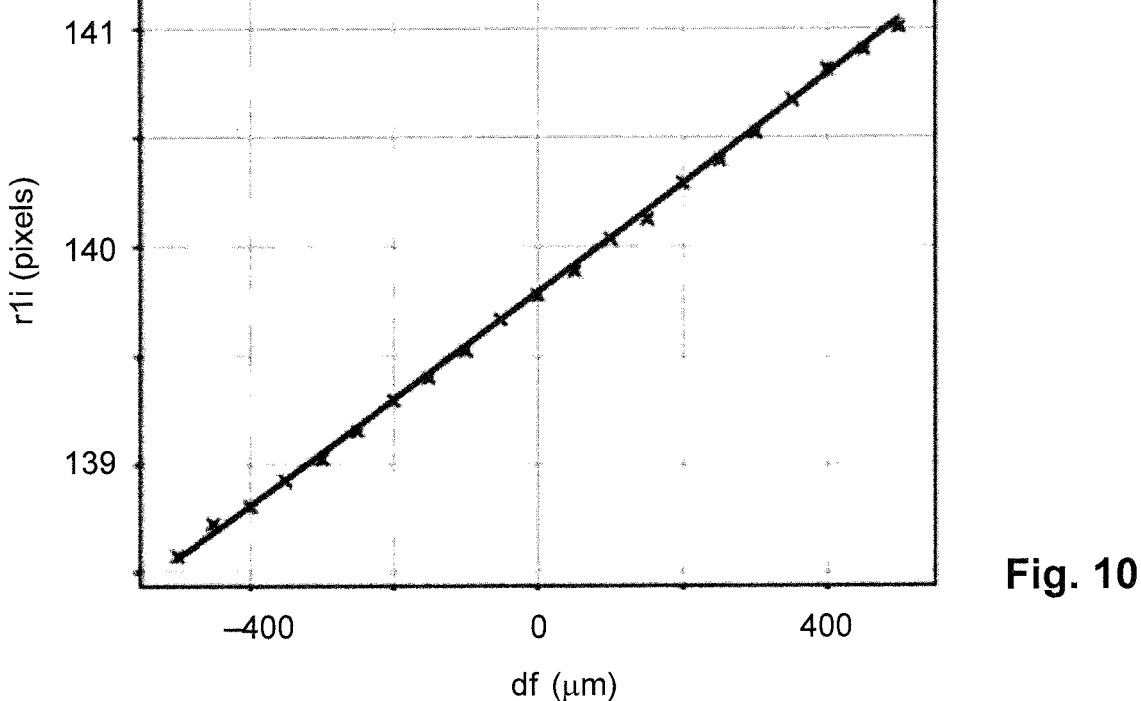

Both these effects lead to change of the radius r1i on the image (FIG. 3) recorded by the camera. In linear approximation, both of them can be accounted for by replacing the constant (ideal) magnification M in Eq. (3) by a corrected value:

$$M = M0 \cdot (1 + df \cdot k) \qquad (4)$$

with M0 being the magnification at ideal focusing, i.e. the magnification in focus plane 34 (M0 can be calibrated or calculated).

k is a scaling factor that can e.g. be obtained by calibration by measuring $r1i$ for a plurality of values of df. This is illustrated in the example of FIG. 10, which shows the dependence of the measured radius $r1i$ as a function of defocusing in such a calibration measurement. The slope of the shown curve can be used to calculate k.

In order to calculate the magnification factor M using Eq. (4), the distance df microscope 6 from its ideal focusing position must be known.

This distance is derived from the radii R1 and R2 of the first and second reflections.

The value of the radii R1, R2 depends on the relative positions of eye 8 and microscope 6 along optical axis 9. This is illustrated in FIG. 4, where the horizontal axis denotes df and the vertical axis the radii.

As can be seen, each radius R1, R2 has a minimum. At this minimum, microscope 6 is at its ideal focusing position for the respective reflection. In the example, it is assumed that df=0 for ideal focusing of the first light sources 15*a*, 15*b*.

Figure 5:
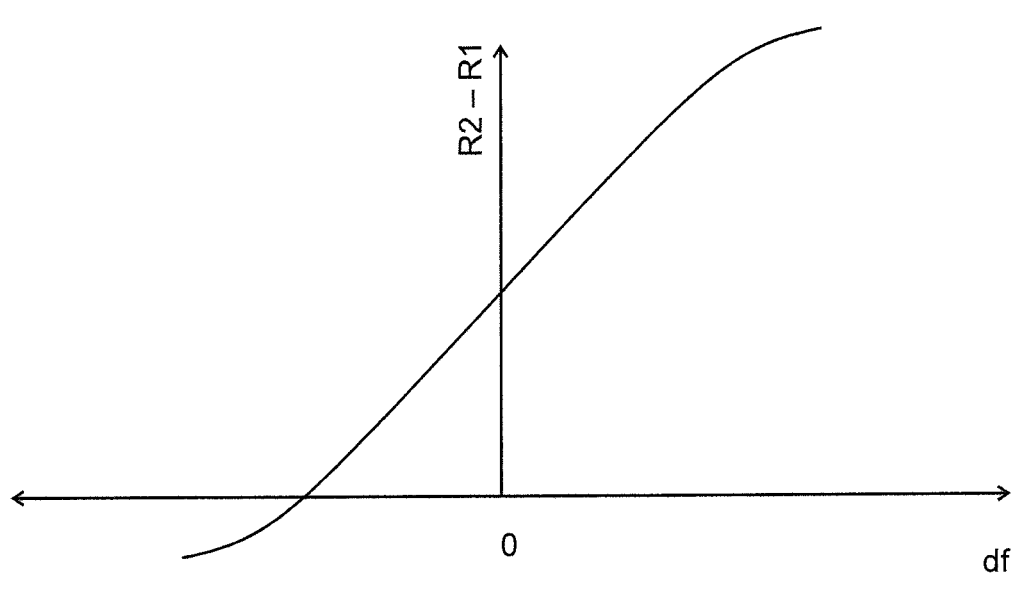
FIG. 5 shows the difference of the radii as a function of the offset of the camera from the ideal focusing distance.

FIG. 5 shows the difference R2−R1 as a function of df. As can be seen, R2−R1 is, around df=0, a monotonous, even substantially linear function.

In linear approximation, df can therefore be estimated from R2−R1 as follows:

$$df=A+B\cdot(R2-R1) \tag{5}$$

The parameters A and B can be obtained from a calibration measurement by recording Purkinje reflections for different microscope distances df around the ideal focusing position.

An alternative to Eq. (5) lies in focusing on one type of reflections and then only using the radius of the other type of reflections for determining df. As it can be seen from FIG. 4, when df is close to 0, R1 varies only slightly while R2 varies strongly and basically linearly. Hence, in a less accurate but potentially still viable approximation, df can be determined from $$df=A'+B'\cdot R2 \tag{5'}$$

The parameters A' and B' can again be obtained from a calibration measurement by recording Purkinje reflections for different microscope distances df around the ideal focusing position.

Instead of the value df, another "distance parameter" may be used, such as g1. (With g1 being estimated from using g1=G1·f0/(r1+G1))

Further, it must be noted that the radii R1, R2 are merely examples of "width parameters" that can be used to describe the size of the reflections. For point light sources or round light sources, another width parameter would be the diameter of the reflections. For other types of light sources, see section "Notes" below.

Measuring R1, R2:

Calculating df (or any other distance parameter) from Eq. (5 or 5') above requires the knowledge of at least radius R2 and optionally also radius R1.

These radii, in pixel coordinates of the image of camera 11, can be calculated using known image processing techniques on the Purkinje image as e.g. shown in FIG. 3.

For example, the individual reflections 20*a*, 20*b*, 21 may be identified and isolated from each other using their position in the image. In a next step, for each reflection, its radius or diameter may be calculated using edge detection.

A particularly robust algorithm is described in the following.

Figure 8:
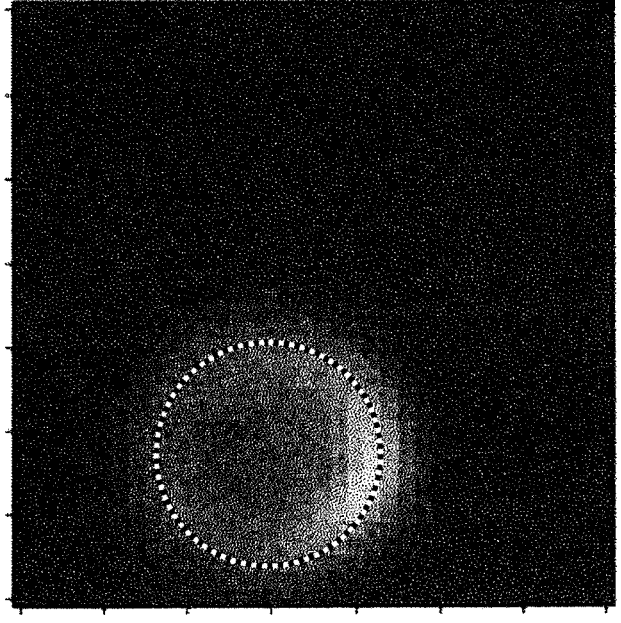
FIG. 8 shows a single second reflection (bright pixels correspond to bright areas; dotted circle indicating edge region)
Figure 9:
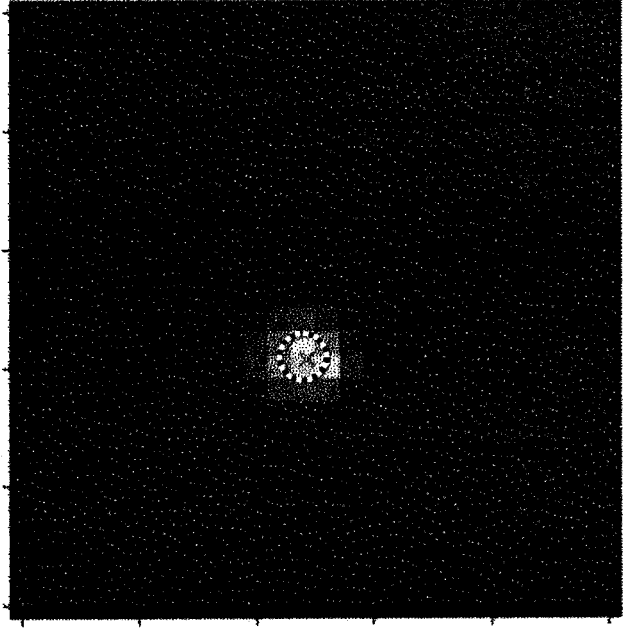
FIG. 9 shows a single first reflection (bright pixels correspond to bright areas; dotted circle indicating Gaussian width), FIG. 10 the ring radius $r1i$ in the reflection image as a function of defocusing in a calibration measurement.

As can be seen from FIGS. 8 and 9, the reflections as recorded by camera 11 may have different structures. For example, the second reflection of FIG. 8 has an asymmetrically bright ring around a somewhat darker center while no internal structure can be recognized for the first reflection in FIG. 9.

It is believed that the structure of the second reflection of FIG. 8 is due to diffraction phenomena in the optical system.

In order to take such effects into account and to use all image pixels of a recorded reflection, fitting models $M_1$, $M_2$ are used to describe the brightness I(x, y) of the first and second reflections as a function of image coordinates x, y), with $$I_i(x,y)=M_i(x,y;c_x,c_y,r,p_1,\ldots p_N) \tag{6}$$

with the following model parameters:

$c_x$, $c_y$: center coordinates i: 1 or 2 for the first or second reflection, r: the model width parameter (corresponding to R1 or R2), $p_1,\ldots p_N$: further model parameters.

Hence, in an advantageous embodiment, the model M1 and/or M2 of the brightness of the first and/or second reflection(s) is fitted to the recorded first and/or second reflection.

To determine the value of the width parameter r (as well as of $c_x$, $c_y$ for calculating the curvature R of the anterior cornea surface), the parameters $c_x$, $c_y$, r, $p_1$, ... $p_N$ are fitted to the image data of a single reflection, such as shown in FIG. 8 or 9, e.g. using a least squares fitting algorithm as known to the skilled person.

For the first reflections, the model $M_1$ can e.g. be a Gaussian with $$M_1(x, y) = A \cdot \exp\left(-\left(\frac{(x - c_x)^2 + (y - c_y)^2}{2r^2}\right)\right) + k0, \tag{7}$$

with k0 being a parameter describing a background offset.

For the second reflections, the model $M_2$ advantageously describes a function that has at least the following properties:

It has a center value at its center point $c_x$, $c_y$ and falls to a background offset (which can be zero) beyond a periphery of the reflection. The periphery is at a distance from center point and given by the width parameter r.

It has, in addition to the width parameter r, the two center point parameters $c_x$, $c_y$ indicative of the position of the center point, an amplitude parameter A indicative of the center value, and at least one edge-height parameter a, b describing the value(s) of the function at the periphery. The values of the function at the periphery can be higher than the center value, at least for some of the edge height parameters a, b. Advantageously, there are two edge-height parameters a, b describing a rotational asymmetry of the value of the function at the periphery around the center point.

The following is a possible example of such a model:

$$M_2(x, y) = A \cdot (u(x, y)G(x, y) + (1 - u(x, y))(c + (1 - c)G(x, y))) \cdot \tag{8}$$

$$(a(x - c_x) + b(y - c_y) + 1) + k0$$

-continued $$u(x, y) = \begin{cases} 1 & \text{für}(x - c_x)^2 + (y - c_y)^2 > r^2 \\ 0 & \text{otherwise} \end{cases}$$

$$G(x, y) = \exp\left(-\left(\frac{(x - c_x)^2 + (y - c_y)^2 - r^2}{\sigma\sqrt{(x - c_x)^2 + (y - c_y)^2 + 1}}\right)^2\right)$$

$\sigma$ describes the width of the ring at the periphery. All the parameters $\sigma$, k0, $c_x$, $c_y$, A, and r are fitted.

Other Applications:

In the example above, the distance parameter df as obtained from the radii R1, R2 was used for refining keratometry measurements, i.e. for determining the curvature R of the anterior cornea surface of eye 8. This curvature R was calculated using the position of the recorded first and/or second reflections 20a, 20b, 21.

The present invention, however, may also be used for measuring other geometric parameters of the eye where the distance between eye 8 and microscope 6 is of importance.

For example, the eye may be illuminated using Placido rings (or by any other defined pattern), and the reflections can be processed to obtain a more detailed model of the cornea's anterior surface.

In another example, the knowledge of the distance parameter df as well as of the curvature R from the measurement above can be used to accurately determine the distance g1 between microscope 6 and the closest part of eye 8. Or it can be used to estimate the distance to other parts of the eye e.g. based on estimates of the size of typical eye structures.

The knowledge of this distance allows to e.g. accurately position the microscope along its optical axis for carrying out quantitative measurements of structures and/or angles, also with a non-telecentric optical system.

Notes:

The calibration measurements described herein can e.g. be carried out on artificial reference samples (e.g. spherical gauges) replacing eye 8.

In the examples above, linear models have been used for device calibration in equations (4), (5), and (6). Higher-order models can be used as well.

In the embodiment shown above, the device is a slit lamp microscope. It must be noted, however, that the device does not require a slit lamp illumination. However, the present technique allows to add improved measurement functionality to conventional slit lamp microscopes.

As mentioned, the light sources of the embodiment above are point light sources (i.e. their extension is much smaller than their distance from the eye, and their features cannot be resolved by microscope 6 even if it is perfectly focused on the light sources).

It must be noted, though, that at least part of the light sources may also be larger, e.g. ring-shaped light sources as they are e.g. used in Placido illumination.

In that case, the width parameter may e.g. be the width of the ring's line.

While there are shown and described presently preferred embodiments of the invention, it is to be distinctly understood that the invention is not limited thereto but may be otherwise variously embodied and practiced within the scope of the following claims.

The invention claimed is:

1. A method for measuring at least one geometric parameter of an eye using a device comprising a microscope on which a first light source and a second light source are attached and a camera that is mounted on the microscope and is coupled to a controller, wherein the first and second light sources are arranged radially outside of an objective of the microscope and are arranged on and movable with the microscope, and wherein the controller is configured to control operation of the first light source, the second light source, the microscope, and the camera, said method comprising:

receiving an instruction from the controller to send first light having a first wavelength from the first light source onto said eye, receiving an instruction from the controller to send second light having a second wavelength different from said first wavelength from the second light source onto said eye, receiving an instruction from the controller to record said eye through said microscope and recording with the camera at least a first reflection at an anterior surface of the eye from said first light and at least a second reflection at the anterior surface of the eye from said second light, the controller measuring at least one of at least a first width parameter indicative of a width of said first reflection or at least a second width parameter indicative of a width of said second reflection, with said at least one of said first or said second width parameter, determining with the controller a distance parameter describing a distance between said microscope and said eye, receiving an instruction from the controller to record a geometry image with the camera related to said geometric parameter and said distance, and calculating said geometric parameter with the controller from said geometry image and said distance parameter.

2. The method of claim 1, wherein said at least one of said first width parameter or said second width parameter is/are indicative of a diameter or radius of said at least first reflection or said at least second reflection.

3. The method of claim 1, wherein, with said at least first width parameter and said at least second width parameter, the distance parameter is determined from a difference between said at least first width parameter and said at least second width parameter.

4. The method of claim 1, wherein said at least first reflection and said at least second reflection are recorded together in a reflection image.

5. The method of claim 1, further comprising focusing said microscope onto the at least first reflection while recording the at least first reflection and the at least second reflection at the anterior surface of the eye.

6. The method of claim 1, further comprising fitting a model of a brightness of said at least first reflection or said at least second reflection to the recorded at least first reflection or the at least second reflection, wherein said at least first width parameter or said at least second width parameter is a model width parameter of said model.

7. The method of claim 6, wherein said model:

describes a function having a center value at a center point and that goes to a background value beyond a periphery at a distance from said center point, wherein said distance depends on said width parameter, and has, in addition to said width parameter, two center point parameters indicative of a position of said center point, an amplitude parameter indicative of said center value, and at least one edge-height parameter, wherein a value of said function at said periphery is higher than said center value for at least some values of said edge-height parameter, and wherein at least said center point parameters, said amplitude parameter and said edge-height parameter(s) are fitted to the recorded reflection.

8. The method of claim 7, wherein said model comprises at least two edge-height parameters describing a rotational asymmetry of a value of said function at said periphery around said center point, wherein both said edge-height parameters are fitted to the recorded reflection.

9. The method of claim 1, wherein said distance parameter is calculated from at least one of said first width parameter or said at least second width parameter using calibration data.

10. A device for measuring at least one geometric parameter of an eye according to the method of claim 1, the device comprising:

a microscope, one or more light sources emitting light at first and second wavelengths, wherein said second wavelength is different from said first wavelength, a camera mounted to said microscope, and a controller.

11. The device of claim 10, wherein said microscope is a non-telecentric microscope.

12. The device of claim 10, wherein at least one of said first wavelength is at least 800 nm or said second wavelength is below 500 nm.

13. The device of claim 10, wherein a diameter of said at least one light source is at least 100 times smaller than the distance between said eye and said microscope.

14. The device of claim 10, wherein said device comprises a plurality of light sources arranged on at least one circle around an optical axis of said microscope.

15. The device of claim 10, wherein said device comprises a plurality of first light sources and wherein said first light sources are arranged on at least first and second concentric circles around an optical axis of the microscope, with at least three of the first light sources on said first circle and at least three of the first light sources on said second circle.

16. The device of claim 10, wherein said light source or light sources is/are arranged radially outside an entry objective of said microscope.

17. The device of claim 10, wherein said geometric parameter is a curvature of said eye, and wherein said curvature is calculated using a position of at least one of said first or second reflections.

18. The device of claim 15, wherein said second light sources are arranged on a third circle.

19. The method of claim 1, wherein a difference between the first wavelength and the second wavelength is at least 100 nm.

20. The method of claim 19, wherein the difference between the first wavelength and the second wavelength is at least 300 nm.

21. The method of claim 4, wherein said reflection image and said geometry image are the same image.

22. The method of claim 9, wherein said distance parameter is calculated from at least one of the first width parameter or the second width parameter using calibration data obtained from measuring the at least one of the first width parameter or the second width parameter for a plurality of distances of the microscope from a reference sample.

23. A method for measuring at least one geometric parameter of an eye using a device comprising a microscope with a first light source, a second light source, and a camera and a control unit, wherein the first and second light sources are arranged radially outside of an objective of the microscope and are arranged on and movable with the microscope, said method being implemented by said control unit and comprising:

sending first light having a first wavelength from the first light source onto said eye, sending second light having a second wavelength different from said first wavelength from the second light source onto said eye, recording an image of said eye through said microscope and recording with the camera at least a first reflection at an anterior surface of the eye from said first light and at least a second reflection at the anterior surface of the eye from said second light, measuring, in said image, at least one of at least a first width parameter indicative of a width of said first reflection and/or at least a second width parameter indicative of a width of said second reflection, with said at least one of said first or said second width parameter, determining with the controller a distance parameter describing a distance between said microscope and said eye, recording a geometry image with the camera related to said geometric parameter and on said distance, and calculating said geometric parameter with the controller from said geometry image and said distance parameter.

24. A method for measuring at least one geometric parameter of an eye using a device comprising a microscope with a first light source, a second light source, a camera and a control unit, wherein the first and second light sources are arranged radially outside of an objective of the microscope and are arranged on and movable with the microscope, said method being performed by said control unit and comprising:

sending first light having a first wavelength from the first light source onto said eye, sending second light having a second wavelength different from said first wavelength from the second light source onto said eye, recording an image of said eye through said microscope and recording with the camera at least a first reflection at an anterior surface of the eye from said first light and at least a second reflection at the anterior surface of the eye from said second light, measuring, in said image, at least one of at least a first width parameter indicative of a width of said first reflection and/or at least a second width parameter indicative of a width of said second reflection, with said at least one of said first or said second width parameter, determining with the controller a distance parameter describing a distance between said microscope and said eye, recording a geometry image with the camera related to said geometric parameter and on said distance, and calculating said geometric parameter with the controller from said geometry image and said distance parameter.

*     *     *     *     *